United States Patent [19]  [11] 4,111,682
Gutman  [45] Sep. 5, 1978

[54] N-(AMINOALKYLENE THIOMETHYL)-N'-(ARYL) UREA HERBICIDES

[75] Inventor: Arnold David Gutman, Berkeley, Calif.

[73] Assignee: Stauffer Chemical Company, Westport, Conn.

[21] Appl. No.: 801,889

[22] Filed: May 31, 1977

Related U.S. Application Data

[63] Continuation of Ser. No. 540,374, Jan. 13, 1975, abandoned.

[51] Int. Cl.$^2$ ............... C07C 127/15; C07C 127/19; A01N 9/12
[52] U.S. Cl. .................. 71/98; 260/553 A; 260/455 R; 560/16; 560/31; 71/100
[58] Field of Search .................. 260/553 A; 71/98

[56] References Cited

U.S. PATENT DOCUMENTS

| | | | |
|---|---|---|---|
| 2,708,677 | 5/1955 | Suter et al. | 260/553 A X |
| 3,072,719 | 1/1963 | Beaver et al. | 260/553 A |
| 3,275,670 | 9/1966 | Skinbrumn et al. | 260/553 A X |
| 3,520,925 | 7/1970 | Koenig et al. | 260/553 A |
| 3,847,971 | 11/1974 | Koenig et al. | 260/553 A X |
| 3,978,123 | 8/1976 | Chan | 260/553 A |
| 3,990,883 | 11/1976 | Clapot et al. | 260/553 A X |
| 4,043,796 | 8/1977 | Hainaut et al. | 71/98 |
| 4,045,209 | 8/1977 | Hainaut et al. | 260/553 A X |

FOREIGN PATENT DOCUMENTS

| | | | |
|---|---|---|---|
| 699,773 | 12/1964 | Canada | 260/553 A |
| 2,256,275 | 5/1973 | Fed. Rep. of Germany. | |
| 1,142,354 | 2/1969 | United Kingdom | 260/553 A |

OTHER PUBLICATIONS

Schuler, CA 68:68660z (1968).
Singer, CA 78:58110n (1973).

*Primary Examiner*—Winston A. Douglas
*Assistant Examiner*—Thomas A. Waltz
*Attorney, Agent, or Firm*—Michael J. Bradley

[57] ABSTRACT

Novel substituted thiomethyl aryl ureas having the formula

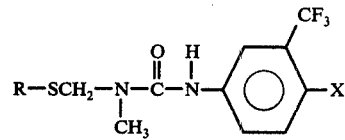

wherein R is selected from the group consisting of alkyl of 1 through 12 carbon atoms; alkenyl containing 2 through 4 carbon atoms;

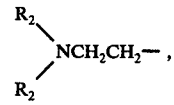

wherein $R_2$ is alkyl containing 1 through 4 carbon atoms;

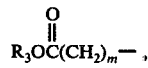

wherein $R_3$ is alkyl containing 1 through 6 carbon atoms and $m$ is 1 or 2;

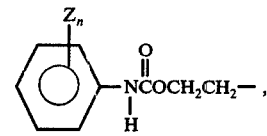

wherein Z is —Cl, —Br, —I, or $CF_3$, and $n$ is a whole number from 1 to 3 inclusive;

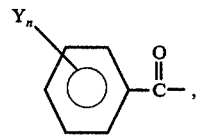

wherein Y is —H, —Cl, —Br, or —I, and $n$ is 1 or 2, and

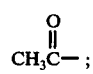

—X is —H or —Cl. The compounds are useful as herbicides.

4 Claims, No Drawings

N-(AMINOALKYLENE THIOMETHYL)-N'-(ARYL) UREA HERBICIDES

This is a continuation of application Ser. No. 540,374 filed Jan. 13, 1975, now abandoned.

BACKGROUND OF THE INVENTION

This invention relates to certain novel compositions and to their use as herbicides. More particularly, the invention relates to certain substituted thiomethyl aryl ureas, and the use of these materials as herbicides.

SUMMARY OF THE INVENTION

The compounds of the invention have the formula

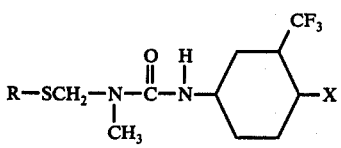

wherein R is selected from the group consisting of alkyl of 1 through 12 carbon atoms; alkenyl containing 2 through 4 carbon atoms;

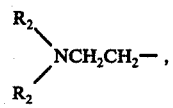

wherein $R_2$ is alkyl containing 1 through 4 carbon atoms;

wherein $R_3$ is alkyl containing 1 through 6 carbon atoms and m is 1 or 2;

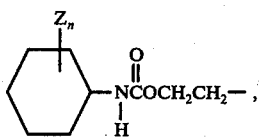

wherein Z is —Cl, —Br, —I, or —CF$_3$, and n is a whole number from 1 to 3 inclusive;

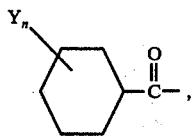

wherein Y is —H, —Cl, —Br, or —I, and n is 1 or 2, and

—X is —H or —Cl. The most preferred compounds of the invention are those, of the formula indicated, wherein R is alkyl of 1 through 8 carbon atoms and X is —H.

In general, the method of the invention comprises contacting undesired vegetation or a locus to be protected with an effective or herbicidal amount of a composition having the formula above indicated.

DETAILED DESCRIPTION OF THE INVENTION

In order to describe the invention with greater particularity, reference is made to the following non-limiting examples. Those skilled in the art will readily recognize the generality of the procedures employed, and will be able thereby to prepare compounds within the scope of the invention which are not specifically described.

EXAMPLE I

Preparation of N-(tert.-butylthiomethyl)-N-methyl amine hydrochloride

Two hundred ml. of acetonitrile and 6.45 g. (0.05 mole) of 1,3,5-trimethylhexahydro-s-triazine are charged to a 500 ml. 3-neck round bottom flask equipped with a stirrer, thermometer and dropping funnel. The mixture is stirred and cooled to −30° C. with a dry ice/acetone bath. Six grams of hydrogen chloride gas are added, followed by slow addition of 13.5 g. (0.15 mole) of tert.-butyl mercaptan dissolved in 50 ml. of acetonitrile. The mixture is then allowed to warm to room temperature and stand overnight.

The following day, the solvent is removed in vacuo. The product is then crystallized by addition of 500 ml. of cold diethyl ether. The solid is collected by filtration, washed with 200 ml. diethyl ether, and dried in a vacuum dessicator. A yield of 23.6 g. (92.8% of theory) of the title compound is obtained.

EXAMPLE II

Preparation of N-methyl-N-(tert.-butylthiomethyl)-N'-(3-trifluoromethylphenyl) urea Two grams of the product of Example I (0.0118 mole), 2.2 g. (0.0118 mole) of 3-trifluoromethylphenylisocyanate, and 100 ml. of acetonitrile are combined in a 250 ml. Erlenmeyer flask. The mixture is magnetically stirred, and 1.9 g. (0.0118 mole) of triethylamine are then added. The resulting mixture is stirred at room temperature for one hour and then poured into 300 ml. of ice water. The crystalline product is collected by filtration and dried to yield 2.0 g. (53% of theory) of the title compound, mp = 96°–99° C. Structure is confirmed by IR and NMR.

EXAMPLE III

Preparation of N-methyl-N-ethylthiomethylamine hydrochloride

Two hundred ml. of acetonitrile, 6.45 g. (0.05 mole) of 1,3,5-trimethylhexahydro-s-triazine; 9.3 g. (0.15 mole) ethyl mercaptan and 6 g. of hydrogen chloride gas are reacted together in the manner of Example I. A yield of 20 g. (95% of theory) of the title compound is obtained.

EXAMPLE IV

Preparation of N-(3-trifluoromethyl)-phenyl-N'-methyl-N'-ethylthiomethyl urea

Five grams (0.0353 mole) of the product of Example III, 6.55 g., (0.0353 mole) of 3-trifluoromethyl phenyl isocyanate; 3.57 g., (0.0353 mole) of triethylamine are reacted together in the manner of Example II. A yield of 9.2 g. (90% of theory) of the title compound is obtained, $N_D^{30}$ - 1.4846. Structure is confirmed by IR and NMR.

EXAMPLE V

Preparation of N-methyl-N-(isopropylmercaptomethyl)-N'-(3-trifluoromethylphenyl urea Three grams of the product of Example III (0.02 mole) 3.7 g. (0.02 mole) of 3-trifluoromethylphenylisocyanate, and 25 ml. of acetonitrile are combined in a 125 ml. Erlenmeyer flask. The mixture is magnetically stirred, and 2.0 g. (0.02 mole) of triethylamine are then added. The resulting mixture is stirred at room temperature for one hour and then poured into 300 ml. of ice water. The crystalline product is collected by filtration and dried to yield 5 g. (82.78% of theory) of the title compound, mp = 76°–78° C. Structure is confirmed by IR and NMR.

EXAMPLE VI

Preparation of N-methyl-N-isopropylthiomethylamine hydrochloride 300 ml. of acetonitrile, 12.9 g. (0.1 mole) of 1,3,5-trimethylhexahydro-s-triazine, 22.8 g. (0.3 mole) of isopropyl mercaptan and 12 g. of hydrogen chloride gas are reacted together in the manner of Example I. A yield of 24.7 g. (52.95% of theory) of the title compound is obtained.

EXAMPLE VII

Preparation of N-methyl-N-tert.-octylthiomethylamine hydrochloride 300 ml. of acetonitrile, 12.9 g. (0.1 mole) of 1,3,5-trimethylhexahydro-s-triazine; 43.8 g. (0.3 mole) of tert.-octylthiomethylamine and 12 g. of hydrogen chloride gas are reacted together in the manner of Example I. A yield of 43.7 g. (64.6% of theory) of the title compound is obtained.

EXAMPLE VIII

Preparation of N-Methyl-N-(tert. octylthiomethyl)-N'-(3-trifluoromethylphenyl) urea Five grams of the product of Example III (0.02 mole), 4.15 g. (0.02 mole) of 3-trifluoromethylphenylisocyanate, and 100 ml. of acetonitrile are combined in a 250 ml. Erlenmeyer flask. The mixture is magnetically stirred, and 2.24 g. (0.02 mole) of triethylamine are then added. The resulting mixture is stirred at room temperature for 1 hour and then poured into 300 ml. of ice water. The crystalline product is collected by filtration and dried to yield 5 g. (59.9% of theory) of the title compound, mp = 52°–54° C. Structure is confirmed by IR and TLC.

TABLE I $$R-SCH_2-N(CH_3)-C(=O)-NH-C_6H_4-X \quad (CF_3)$$

| Compound Number | R | X | Physical Properties |
|---|---|---|---|
| 1 | $C_2H_5-$ | Cl— | $N_D^{30} - 1.5387$ |
| 2 | $(CH_3)_2CH-$ | H— | mp. 76 – 78° C |

TABLE I-continued $$R-SCH_2-N(CH_3)-C(=O)-NH-C_6H_4-X \quad (CF_3)$$

| Compound Number | R | X | Physical Properties |
|---|---|---|---|
| 3 | $(CH_3)_3C-$ | H— | mp. 96 – 99° C |
| 4 | $(CH_3)_3CCH_2(CH_3)_2C-$ | H— | $N_D^{30} - 1.4760$ |
| 5 | $CH_3(CH_2)_6CH_2-$ | H— | $N_D^{30} - 1.4712$ |
| 6 | $C_6H_5C(=O)-$ | H— | |
| 7 | $(C_2H_5)_2NCH_2CH_2-$ | H— | $N_D^{30} - 1.4760$ |
| 8 | $CH_3OC(=O)CH_2CH_2-$ | H— | $N_D^{30} - 1.4820$ |
| 9 | $C_2H_5-$ | H— | $N_D^{30} - 1.4846$ |
| 10 | $C_2H_5OC(=O)CH_2-$ | H— | $N_D^{30} - 1.4843$ |
| 11 | $n-C_3H_7-$ | H— | mp. 60 – 64° C |
| 12 | $i-C_3H_7$ | Cl— | $N_D^{30} - 1.4752$ |
| 13 | $(CH_3)_3C-$ | Cl— | $N_D^{30} - 1.4883$ |
| 14 | $C_8H_{17}-$ | Cl— | $N_D^{30} - 1.4718$ |
| 15 | $(CH_3)_3CCH_2(CH_3)_2C-$ | Cl— | $N_D^{30} - 1.4848$ |
| 16 | $C_2H_5OC(=O)CH_2-$ | Cl— | $N_D^{30} - 1.4878$ |
| 17 | $CH_3$ | H— | $N_D^{30} - 1.4760$ |
| 18 | $n-C_3H_7-$ | Cl— | $N_D^{30} - 1.4970$ |
| 19 | $n-C_4H_9OC(=O)CH_2-$ | Cl— | $N_D^{30} - 1.4914$ |
| 20 | $n-C_4H_9OC(=O)CH_2$ | H— | $N_D^{30} - 1.4750$ |
| 21 | $CH_3-$ | Cl— | $N_D^{30} - 1.5030$ |
| 22 | $(CH_3)_2CHCH_2CH_2-$ | H— | $N_D^{30} - 1.4743$ |
| 23 | $(CH_3)_2CHCH_2CH_2-$ | Cl— | $N_D^{30} - 1.4885$ |
| 24 | $CH_3(CH_2)_{10}CH_2-$ | H— | mp. 34 – 37° C |
| 25 | $CH_3(CH_2)_{10}CH_2-$ | Cl— | $N_D^{30} - 1.4780$ |

As indicated, the compositions of the invention are phytotoxic compounds which are useful in controlling various plant species. Several of the compounds of the invention were tested as herbicides in the following manner.

A. Pre-emergence Screening Test: A fiber flat which is 7 inches long, 5 inches wide and 2.5 inches deep is filled to a depth of 2 inches with loamy sand soil. Seeds of seven different weed species are planted in individual rows, using one species per row across the width of the flat. The seeds are covered with soil so that they are planted at a depth of 0.5 inch. The seeds used are hairy crabgrass (*Digitaria sanguinalis*), foxtail (*Setaria spp.*), watergrass (*Echinochloa crusgalli*), red oat (*avena sativa*), redroot pigweed (Amaranthus retroflexus), mustard (*Brassica juncea*) and curly dock (*Rumex crispus*). Ample seeds are planted to give about 20 to 50 seedlings per row after emergence depending on the size of the plants.

The next day, about 20 mg. of the compound to be tested are weighed and placed in a 300 ml. wide-mouth bottle. About 3 ml. of acetone containing 1% Tween 20[R] is added to dissolve the compound. If the material is not soluble in acetone, another solvent such as water, alcohol or dimethylformamide (DMF) is used. When DMF is used, only 0.5 ml. or less is used to dissolve the compound and then another solvent is used to make the volume up to 3 ml. The 3 ml. of solution are sprayed uniformly on the soil contained in the Fiber Flat. A No. 152 DeVilbiss atomizer, which used compressed air at a pressure of 5 lb/sq. in. is used to apply the spray. The rate of application is 8 lb/acre and the spray volume is 143 gal/acre. This procedure is followed with each of the compounds tested.

After treatment the flats are placed in the greenhouse at a temperature of 70° to 85° F. and watered by sprinkling. Two and one-half weeks after treatment the degree of injury or control is determined by comparison with untreated check plants of the same age. The injury rating from 0 to 100% is recorded for each species as percent control with 0% representing no injury and 100% representing complete kill. The results of the test are shown in Table II.

TABLE II

| Compound Number | Crab-grass | Fox-tail | Water-grass | Red Oat | Pig-weed | Mus-tard | Curly Dock |
|---|---|---|---|---|---|---|---|
| 1 | 100 | 98 | 70 | 60 | 98 | 100 | 80 |
| 2 | 98 | 100 | 100 | 98 | 100 | 100 | 100 |
| 3 | 100 | 100 | 100 | 90 | 100 | 90 | 90 |
| 4 | 90 | 90 | 95 | 80 | 90 | 100 | 98 |
| 5 | 95 | 95 | 100 | 90 | 100 | 100 | 98 |
| 6 | 100 | 100 | 100 | 100 | 100 | 100 | 100 |
| 7 | 30 | 0 | 20 | 10 | 0 | 50 | 0 |
| 8 | 80 | 80 | 70 | 60 | 70 | 80 | 80 |
| 9 | 80 | 90 | 100 | 70 | 80 | 90 | 90 |
| 10 | 60 | 70 | 80 | 50 | 50 | 100 | 60 |
| 11 | 90 | 95 | 100 | 80 | 70 | 80 | 70 |
| 12 | 70 | 60 | 50 | 40 | 90 | 100 | 80 |
| 13 | 20 | 0 | 20 | 20 | 80 | 100 | 80 |
| 14 | 0 | 0 | 0 | 0 | 40 | 20 | 20 |
| 15 | 10 | 50 | 40 | 70 | 80 | 100 | 80 |
| 16 | 0 | 0 | 10 | 20 | 0 | 50 | 0 |
| 17 | 20 | 0 | 50 | 40 | 80 | 90 | 20 |
| 18 | 20 | 20 | 20 | 40 | 100 | 100 | 70 |
| 19 | 0 | 0 | 0 | 0 | 0 | 60 | 0 |
| 20 | 50 | 50 | 70 | 70 | 0 | 100 | 70 |
| 21 | 90 | 100 | 80 | 80 | 100 | 100 | 100 |
| 22 | 100 | 100 | 100 | 60 | 80 | 100 | 100 |
| 23 | 70 | 80 | 40 | 0 | 80 | 100 | 100 |
| 24 | 60 | 60 | 20 | 20 | 0 | 70 | 60 |

B. Postemergence Herbicide Screening Test: Seeds of six plant species, including hairy crabgrass, watergrass, red oat, mustard, curly dock and Pinto beans (*Phaseolus vulgaris*) are planted in the fiber flats as described above for preemergence screening. The flats are placed in the greenhouse at 70 to 85° F. and watered daily with a sprinkler. About 8 to 12 days after planting, when the primary leaves of the bean plants are almost fully expanded and the first trifoliate leaves are just starting to form, the plants are sprayed. The spray is prepared by weighing out 20 mg. of the test compound, dissolving it in 5 ml. of acetone containing 1% Tween 20, and then adding 5 ml. of water. The solution is sprayed on the foliage using a No. 152 DeVilbiss atomizer at an air pressure of 5 lb/sq. in. The spray concentration is 0.2 and the rate is 8 lb/acre. The spray volume is 476 gal/acre. Results of the tests are shown in Table III.

TABLE III

| Compound Number | Crab-grass | Water grass | Red Oat | Mustard | Curly Dock | Pinto Beans |
|---|---|---|---|---|---|---|
| 1 | 99 | 99 | 100 | 100 | 99 | 100 |
| 2 | 100 | 100 | 95 | 100 | 100 | 100 |
| 3 | 100 | 100 | 100 | 100 | 100 | 100 |
| 4 | 100 | 100 | 100 | 100 | 100 | 100 |
| 5 | 100 | 100 | 100 | 100 | 100 | 100 |
| 6 | 100 | 100 | 100 | 100 | 100 | 100 |
| 7 | 100 | 100 | 100 | 100 | 100 | 80 |
| 8 | 100 | 100 | 100 | 100 | 100 | 100 |
| 9 | 100 | 100 | 100 | 100 | 100 | 100 |
| 10 | 100 | 100 | 100 | 100 | 100 | 100 |
| 11 | 100 | 100 | 100 | 100 | 100 | 100 |
| 12 | 98 | 100 | 100 | 100 | 100 | 100 |
| 13 | 100 | 100 | 100 | 100 | 100 | 100 |
| 14 | 100 | 100 | 100 | 100 | 100 | 100 |
| 15 | 98 | 100 | 100 | 100 | 100 | 100 |

TABLE III-continued

| Compound Number | Crab-grass | Water grass | Red Oat | Mustard | Curly Dock | Pinto Beans |
|---|---|---|---|---|---|---|
| 16 | 100 | 100 | 100 | 100 | 100 | 100 |
| 17 | 100 | 100 | 100 | 100 | 100 | 100 |
| 18 | 100 | 100 | 100 | 100 | 100 | 100 |
| 19 | 100 | 100 | 100 | 100 | 100 | 100 |
| 20 | 98 | 100 | 100 | 100 | 100 | 100 |
| 21 | 100 | 100 | 100 | 100 | 100 | 100 |
| 22 | 100 | 100 | 100 | 100 | 100 | 100 |
| 23 | 100 | 100 | 100 | 100 | 100 | 100 |
| 24 | 100 | 100 | 100 | 100 | 100 | 100 |
| 25 | 100 | 100 | 70 | 100 | 100 | 100 |

As can be seen by the test results, the compounds of the invention are useful as herbicides. Moreover, the compounds of this invention have high tolerance to valuable crops such as cotton. They may be applied directly to the particular undesired plant species or may be applied to a locus to be protected. In either event, it is, of course, necessary that the unwanted species receive an effective dosage of amount, i.e., an amount sufficient to kill or retard growth.

The compounds are normally employed with a suitable carrier and may be applied as a dust, spray, drench or aerosol. The compounds thus may be applied in combination with solvents, diluents, various surfact active agents (for example, detergents, soaps or other emulsifying or wetting agents, surface active clays), carrier media, adhesives, spreading agents, humectants and the like. They may also be combined with other biologically active compositions, including other herbicides, fungicides, bactericides and algaecides, insecticides, growth stimulators, acaricides, molluscicides, etc., as well as with fertilizers, soil modifiers, etc. The compounds of the invention may be used in combination with an inert carrier and a surface active or emulsifying agent and may also be applied in combination with other biologically active materials, in conjunction with a carrier and a surface active or emulsifying agent. The solid and liquid formulations can be prepared by any of the conventional methods well known by those skilled in the art. Determination of the optimum effective concentration for a specific application is readily conducted by routine procedures, as will be apparent to those skilled in the art. As indicated, the amount applied in a given case will be an effective amount, i.e., an amount sufficient to give the type of control desired.

Various changes and modifications may be made without departing from the spirit and the scope of the invention described herein, as will be apparent to those skilled in the art to which it pertains.

What is claimed is:

1. A compound having the formula

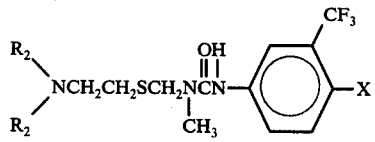

wherein $R_2$ is alkyl containing 1 through 4 carbon atoms and X is selected from the group consisting of hydrogen and chlorine.

2. The compound of claim 1 in which $R_2$ is —$C_2H_5$.

3. The method of controlling weed species by applying to the habitat of said weed species to be controlled an effective amount of a compound having the formula
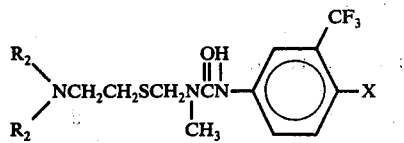
wherein $R_2$ is alkyl containing 1 through 4 carbon atoms and X is selected from the group consisting of hydrogen and chlorine.
4. The compound of claim 3 wherein $R_2$ is $-C_2H_5$.

UNITED STATES PATENT AND TRADEMARK OFFICE
CERTIFICATE OF CORRECTION

PATENT NO. : 4,111,682   Page 1 of 2
DATED : September 5, 1978
INVENTOR(S) : Arnold D. Gutman It is certified that error appears in the above-identified patent and that said Letters Patent are hereby corrected as shown below:

Column 1, line 20, formula should be

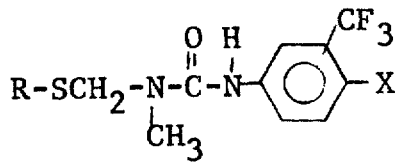

Column 1, line 45, formula should be

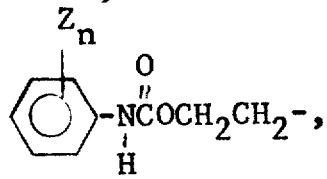

Column 1, line 55, formula should be

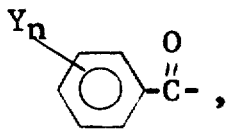

UNITED STATES PATENT AND TRADEMARK OFFICE
CERTIFICATE OF CORRECTION

PATENT NO. : 4,111,682   Page 2 of 2
DATED : September 5, 1978
INVENTOR(S) : Arnold D. Gutman It is certified that error appears in the above-identified patent and that said Letters Patent are hereby corrected as shown below:

Column 3, line 63, the formula should be

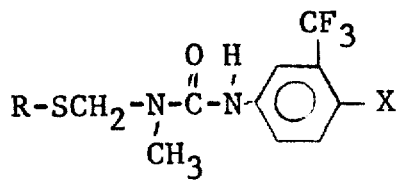

Column 4, line 5, the formula should be

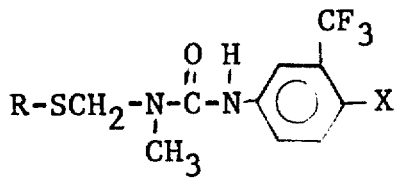

Signed and Sealed this

Eighteenth Day of September 1979

[SEAL]

Attest:

LUTRELLE F. PARKER
Attesting Officer   Acting Commissioner of Patents and Trademarks